United States Patent [19]

Buican

[11] Patent Number: 5,208,651
[45] Date of Patent: May 4, 1993

[54] APPARATUS AND METHOD FOR MEASURING FLUORESCENCE INTENSITIES AT A PLURALITY OF WAVELENGTHS AND LIFETIMES

[75] Inventor: Tudor N. Buican, Albuquerque, N. Mex.

[73] Assignee: The Regents of the University of California, Alameda, Calif.

[21] Appl. No.: 731,070

[22] Filed: Jul. 16, 1991

[51] Int. Cl.$^5$ ............................................. G01B 9/02
[52] U.S. Cl. ................................... 356/346; 356/351
[58] Field of Search ............... 356/345, 346, 351, 352; 250/458.1, 461.2

[56] References Cited

U.S. PATENT DOCUMENTS

| | | | |
|---|---|---|---|
| 3,984,190 | 10/1976 | Ballett et al. | 356/346 |
| 4,905,169 | 2/1990 | Buican et al. | 356/346 |
| 4,983,041 | 1/1991 | Inaba | 356/346 |
| 4,999,013 | 3/1991 | Zoechbauer et al. | 356/346 |

OTHER PUBLICATIONS

Tudor N. Buican, "Real-Time Fourier Transform Spectrometry for Fluorescence Imaging and Flow Cytometry", *Bioimaging and Two-Dimensional Spectroscopy*, Louis C. Smith, Ed. (SPIE, Los Angeles, CA, 1990), vol. 1205, pp. 126–133.

*Primary Examiner*—Samuel A. Turner
*Attorney, Agent, or Firm*—Samuel M. Freund; Paul D. Gaetjens

[57] ABSTRACT

Apparatus and method for measuring intensities at a plurality of wavelengths and lifetimes. A source of multiple-wavelength electromagnetic radiation is passed through a first interferometer modulated at a first frequency, the output thereof being directed into a sample to be investigated. The light emitted from the sample as a result of the interaction thereof with the excitation radiation is directed into a second interferometer modulated at a second frequency, and the output detected and analyzed. In this manner excitation, emission, and lifetime information may be obtained for a multiplicity of fluorochomes in the sample.

17 Claims, 4 Drawing Sheets

APPARATUS AND METHOD FOR MEASURING FLUORESCENCE INTENSITIES AT A PLURALITY OF WAVELENGTHS AND LIFETIMES

The U.S. Government has rights in this invention under Contract No. W-7405-ENG-36 between the U.S. Department of Energy and the Regents of the University of California.

BACKGROUND OF THE INVENTION

The invention described herein relates generally to structures and methods for performing fluorescence analyses of single particles and assemblies of particles, and more particularly to apparatus and methods for simultaneously measuring fluorescence intensities at a plurality of excitation and emission wavelengths, and at a plurality of fluorescence lifetimes of single particles and assemblies of particles both locally and remotely.

The ability to extract fluorescence signals from a background on the basis of specific excitation, emission and lifetime properties of fluorochromes is essential in such diverse fields as cytometry and lidar-based remote detection. The invention presented in this disclosure concerns a method and the corresponding apparatus for extracting specific fluorescence signals in real time from a light background, the extraction process simultaneously making use of specific excitation, emission and lifetime properties of the fluorochromes.

Much flow cytometric and imaging work in biology is concerned with the quantitation of probes that bind in a specific manner to various biological structures. Such probes are usually fluorescent (either intrinsically or through the chemical attachment of fluorescent molecules), and can thus be detected by flow and imaging analytical instruments through optical and photometric means.

It is preferable in many such applications to use several, simultaneous probes. The simultaneous presence of a range of probes of different specificities may reveal, if the probes can be independently quantitated, a correlated picture of the distribution of several biochemical determinants in a cell population (flow cytometry) or inside a cell or tissue (fluorescence microscopy). If the probes are fluorescent and the fluorescence of each probe has distinctive properties (in terms of its excitation and emission spectra, as well as of its fluorescence lifetime spectrum), then these properties may be used by an analytical instrument in order to separate the contributions of the different probes to the total fluorescence, and thus independently quantitate the various probes.

Previous approaches to the problem of fluorochrome separation have used different optical and data-processing techniques for each set of fluorescence properties (excitation, emission, and lifetime). Of these, the techniques for measuring excitation and emission properties are, however, similar. In general, they are based on the spatial or temporal division of the excitation and emission spectra into a number of spectral channels, the measurement of the fluorescence intensity being correlated in space and/or time with the excitation and emission spectral channels. For example, in fluorescence microscopy, there may be several excitation and emission filters mounted on filter wheels, with fluorescence intensity measurement being successively made for various combinations of filters. In flow cytometers, different excitation wavelengths may be provided at different locations along the particle-carrying stream by different laser beams, thus providing a temporal sequence of excitation wavelengths for particles in the stream. The emission spectrum is spatially divided into regions of interest by combinations of optical filters and partially reflecting surfaces, with one detector for each spectral region.

Measurements of fluorescence lifetime are usually based on modulation techniques, whereby the intensity of the excitation light is temporally modulated according to some modulation scheme (harmonic, multiharmonic, periodic sequence of narrow pulses), and the lifetime information is extracted from the shape of the emission intensity waveform. A lifetime measurement in flow has yet to be demonstrated. In imaging systems, measurements have been performed for long-lived, delayed fluorescence or phosphorescence.

Another field in which a fluorescence signal must be extracted from a background is that of fluorescence lidar. For example, the remote detection and mapping of the distribution of biological aerosols can be achieved by projecting a pulsed laser beam of appropriate wavelength into the atmosphere and detecting the fluorescence emitted by tryptophan, an ubiquitous component of proteins. If the tryptophan fluorescence signal can be extracted from the background light, then the distribution of delays between the excitation laser pulse and the fluorescence signals can be used to map the spatial distribution of the aerosol.

The use of specific excitation and emission properties of fluorochromes to be detected by lidar are useful in extracting their fluorescence signals from the background. The lifetime properties are often more useful, especially if one is measuring the fluorescence intensity time-response function. In this situation, the fluorochrome's characteristic fluorescence decay is shifted in time by an amount equal to the sum of the propagation times for the excitation and fluorescence pulses. Thus, the fluorescence time-response function contains information on both lifetime and distance. The two can be easily separated if the lifetime is much shorter than the propagation delay, which is typically the case in fluorescence lidar applications.

Accordingly, it is an object of the present invention to provide an apparatus and method for allowing the simultaneous measurement of excitation, emission and lifetime properties of fluorochromes using a single, integrated instrument.

Another object of the invention is to provide an apparatus and method for allowing the remote, simultaneous measurement of excitation, emission and lifetime properties, and the spatial distribution of fluorochromes using a single, integrated instrument.

Yet another object of the present invention is to provide an apparatus and method for allowing the simultaneous measurement of excitation, emission and lifetime properties of fluorochromes in single particles using a single, integrated instrument.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the apparatus for simultaneously measuring any combination of excitation, emission, and lifetime properties of the fluorescence from a sample includes an excitation light source having a source of multiple-wavelength electromagnetic radiation, the output of which is directed into a first interferometer, the combination providing a chosen plurality of excitation wavelengths, each excitation wavelength being modulated at a multiplicity of frequencies different from those of other wavelengths within the plurality thereof, which is directed into the sample, a second interferometer for receiving electromagnetic radiation emitted from the sample resulting from the interaction thereof with the excitation light, whereby each received wavelength is modulated at a multiplicity of frequencies different from those of other received wavelengths before appearing as an output therefrom, a detector for receiving the output from the second interferometer and for generating an electrical signal therefrom, and means for analyzing the electrical signal from the detector and for deriving any combination of the fluorescence properties of the sample.

In a further aspect of the present invention, in accordance with its objects and purposes, the apparatus for simultaneously measuring any combination of excitation, emission, and lifetime properties of the fluorescence from a sample includes an excitation light source having a source of multiple-wavelength electromagnetic radiation, the output of which is directed into an interferometer, the combination thereof providing a chosen plurality of excitation wavelengths, each excitation wavelength being modulated at a multiplicity of frequencies different from those of other wavelengths within the plurality thereof, which is directed into the sample, apparatus for collecting electromagnetic radiation emitted from the sample resulting from the interaction thereof with the light from the excitation source, and for directing this light back into the interferometer, whereby modulation is introduced into the emitted electromagnetic radiation such that each emitted wavelength is modulated at a multiplicity of frequencies different from those of other emitted wavelengths before appearing as a second output therefrom, a detector for receiving the second output from the interferometer and for generating an electrical signal therefrom, and means for analyzing the electrical signal from the detector and for deriving therefrom any combination of the fluorescence properties of the sample.

In yet a further aspect of the present invention, in accordance with its objects and purposes, the method for simultaneously measuring any combination of excitation, emission, and lifetime properties of the fluorescence from a sample, includes exciting the sample with electromagnetic radiation having a chosen plurality of excitation wavelengths, each excitation wavelength being modulated at a multiplicity of frequencies different from those of other wavelengths within the plurality thereof, collecting the light emitted from the sample resulting from the interaction thereof with the plurality of excitation wavelengths, introducing modulation into the collected emitted electromagnetic radiation such that each collected wavelength is modulated at a multiplicity of frequencies different from those of other collected wavelengths, detecting the modulated, collected emitted electromagnetic radiation and generating an electrical signal therefrom, and analyzing the electrical signal to derive therefrom any combination of the fluorescence properties of the sample.

Benefits and advantages of our invention include: (i) the treatment of all three fluorescence parameters in a homogeneous manner using the same optical and data processing components, whereby high-speed trivariate spectral analyses (less than 6 $\mu$s using currently available technology) can be achieved for local and remote samples; (ii) the homogeneous processing of the data in the three variables has the result that total fluorescence can be resolved into contributions from different fluorochromes on the basis of differences in any of the three fluorescence parameters in both flow and imaging instruments, which in turn leads to considerably higher analytical potential with simultaneous analysis of higher numbers of fluorescent probes being possible despite overlapping spectral characteristics; and (iii) the elimination of short excitation pulses for application of the present invention to lidar, thereby allowing a high-duty-cycle excitation signal to be used.

BRIEF DESCRIPTION OF THE DRAWINGS

The accompanying drawings, which are incorporated in and form a part of the specification, illustrate two embodiments of the present invention and, together with the description, serve to explain the principles of the invention.

FIG. 4 shows schematic representations of optical configurations for three applications of the trivariate Fourier transform spectrometer of the present invention illustrated in FIG. 2 hereof.

DETAILED DESCRIPTION OF THE PREFERRED EMBODIMENTS OF THE INVENTION

Figure 1:
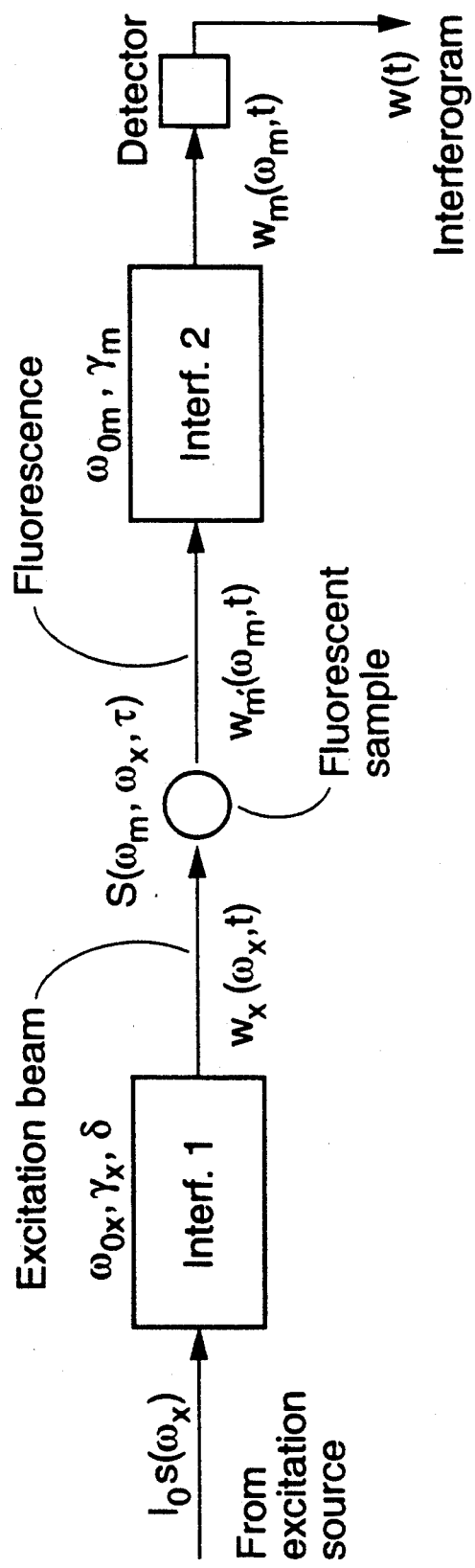
FIG. 1 is a generalized representation of the two-interferometer apparatus of the present invention, associating the important parameters with the elements of the apparatus with which they are related.

Briefly, the present invention includes an apparatus and method for allowing the simultaneous measurement of excitation, emission and lifetime properties of fluorochromes using a single, integrated instrument. The approach used in solving this problem represents an expansion of the Fourier transform techniques for emission and excitation spectrometry described in U.S. Pat. No. 4,905,169, for "Method And Apparatus For Simultaneously Measuring A Plurality Of Spectral Wavelengths Present In Electromagnetic Radiation," issued to Tudor N. Buican and John C. Martin on Feb. 27, 1990, the disclosure thereof hereby being incorporated by reference herein, applied to the more general situation. The present invention includes a high-speed Fourier transform spectrometer useful for analyzing the emission or excitation spectra of fluorochromes in flow.

With minor additions, the same apparatus may be used for a pixel-by-pixel spectral analysis in a fluorescence imaging system as well as for lidar. The Fourier transform spectrometer has high throughput, high speed of analysis, and can resolve large numbers of fluorochromes on the basis of their emission or absorption properties.

The spectrometer is based on a birefringent interferometer, for example, such as that described in "Real-Time Fourier Transform Spectrometry For Fluorescence Imaging And Flow Cytometry," by Tudor N. Buican, pages 126–133, Proceedings of the SPIE, Vol. 1205, January, 1990, the teachings thereof hereby being incorporated by reference herein, and the interferograms are obtained as functions of time that modulate the instantaneous intensity of the light passing through the interferometer. It is this ability of the interferometer to modulate, at high frequencies, the intensity of light according to a waveform that is related by a mathematical transformation to the spectrum of the light, that allows this type of instrument to analyze not just frequency (wavelength) spectra, but also lifetime distributions. Furthermore, the information in suitably collected interferograms can be processed in real-time to yield a trivariate fluorescence intensity the simultaneous variables being the excitation and emission frequencies, and the fluorescence delay.

Transform spectrometry is based upon the principle that some physical device, such as an interferometer, may be used to encode one functional dependence of a measured parameter into another, the latter functional dependence being chosen so as to be more readily recorded than the former. Clearly, a decoding scheme must exist, so that the desired functional dependence may be retrieved from the experimentally recorded one. In many situations, physical limitations in the encoding or recording process result in imperfect decoding, which leads to the retrieved functional dependence being an approximation of the actual one. Fourier transform spectrometers use interferometers in order to encode the wavelength dependence of the light intensity into a spatial or temporal distribution of that intensity (interferogram). As the encoding scheme is a Fourier transform, decoding (i.e., retrieval of the spectral information from the interferogram) is based on the inverse Fourier transform. The most important physical limitation in this case is the fact that only a finite segment of the interferogram can be recorded. This results in limited spectral resolution and, possibly, in spurious spectral features.

In general, a transform instrument can be specified by providing the following:
1. The physical device that performs the transform, and a mathematical description of that (direct) transform;
2. A mathematical description of the inverse transform; and
3. A mathematical description of the response function.

As stated, physical limitations may cause the direct transform not to have an exact inverse. In such a case, the inverse transform is only approximate, in the sense that its result may itself be a transform of the original spectrum. This latter transform is generally defined by the instrument's response function. Furthermore, the inverse transform (and, therefore, the response function), may not be unique, the choice of inverse transform being generally dictated by the choice of response function.

Reference will now be made in detail to the present preferred embodiment of the invention, and example of which is illustrated in the accompanying drawing. FIG. 1 is a generalized representation of the two-interferometer apparatus of the present invention. In describing the theoretical basis for the invention, assume that the excitation, emission and fetime properties of a system of fluorochromes is described by a function, $S(\omega_m, \omega_x, \tau)$, such that the spectral intensity of the emitted light, $w_m(\omega_m, t)$, is related to they spectral intensity of the excitation light, $w_x(\omega_x, t)$ through the following transformation:

$$w_m(\omega_m, t) = \int_0^\infty d\omega_x \int_0^\infty d\tau S(\omega_m, \omega_x, \tau) W_x(\omega_x, t - \tau)$$

The function, $S(\omega_m, \omega_x, \tau)$, is identified as the spectral time-response function of the system of fluorochromes, as it describes the fraction of the excitation intensity in the spectral interval, $(\omega_x, \omega_x + d\omega_x)$, that is emitted in the spectral interval, $(\omega_m, \omega_m + d\omega_m)$, after a delay between $\tau$ and $\tau + d\tau$. The above transformation is linear and thus only holds if the fluorochrome system is far from saturation.

FIG. 1 shows the generalized two-interferometer apparatus for trivariate Fourier transform fluorescence spectrometry of the present invention, and includes two interferometers that are harmonically driven at two different frequencies. Interferometers, 1 and 2 are excitation and emission interferometers respectively; $s_x(\omega_x)$ is the spectrum of the excitation beam; $S(\omega_x, \omega_m, \sigma)$, the trivariate fluorescence response function of the sample; $w_m(\omega_x, t)$ the excitation interferogram; $w_m'(\omega_m, t)$ the emission interferogram before emission interferometer; $w_m(\omega_m, t)$, the emission interferogram after the emission interferometer; $\omega_{Ox}$ and $\gamma_x$, the driving frequency and modulation amplitude of the excitation interferometer; $\omega_{Om}$ and $\gamma_m$, the driving frequency and modulation amplitude of the emission interferometer, respectively; and $\delta$ is the initial phase difference between the two interferometers. The preferred embodiments of these interferometers are described in the references, supra. A polychromatic excitation beam intensity, $I_O$, and normalized spectrum, $s(\omega_x)$, passes through the first interferometer and strikes the fluorescent sample. The emitted fluorescence is collected and passes through the second interferometer, following which it strikes a detector. The two interferometers are driven, respectively, at frequencies $\omega_{Ox}$ and $\omega_{Om}$, and with modulation amplitudes $\gamma_x$ and $\gamma_m$, respectively. Although the two interferometer driving frequencies are arbitrary, a preferred embodiment is that in which the driving frequency of one interferometer is an integer multiple of the other's, $\omega_{Ox} = n\omega_{Om}$. This embodiment makes the synchronization of the data acquisition and processing system easier, as a single phase reference signal needs to be used in order to generate the data acquisition clock signal. It can be shown that the interferogram, w(t), can be derived from the spectral time-response function through a linear transform. Furthermore, it can be shown that the spectral time-response function can be reconstructed from the interferogram.

As the interferogram is a linear transformation of the spectral time-response function that preserves the differences between the excitation, emission and lifetime properties of the fluorochromes (after convolution with a point-response function that sets an upper limit on the resolution of the method), individual fluorochrome contributions to the total fluorescence can be obtained from the total interferogram if the characteristic interferograms for the individual fluorochromes are known. This procedure is detailed in the Buican Journal article supra. Thus, the same type of data acquisition and real-time processing that was developed for emission Fourier transform instruments can also be used in the trivariate Fourier transform apparatus of the present invention.

Typical fluorescence lifetimes of several nanoseconds or less correspond to distances of 1 m or less. Thus, the spectral time-response function in lidar applications will appear as a very narrow pulse at an angular distance from the origin of $2\omega_{Ox}D/c$, where D is the distance to the fluorescent sample and c is the speed of light. An extended distance distribution will be mirrored, up to a simple function of distance, by the time-response function. The maximum range allowed by aliasing is $\pi c/2\omega_{Ox}$ which, for a driving frequency of 50 kHz, yields a maximum distance of 1.5 km. Taking aliasing (avoidance of signal distortion in the reconstructed signal and uncovered distance mapping) into account, the previous figure becomes the maximum thickness of the region that can be mapped. The spatial resolution of the lidar is determined by the width of the point-response function, which is inversely proportional to the retardation amplitude of the excitation interferometer, $\gamma_x$.

Figure 2:
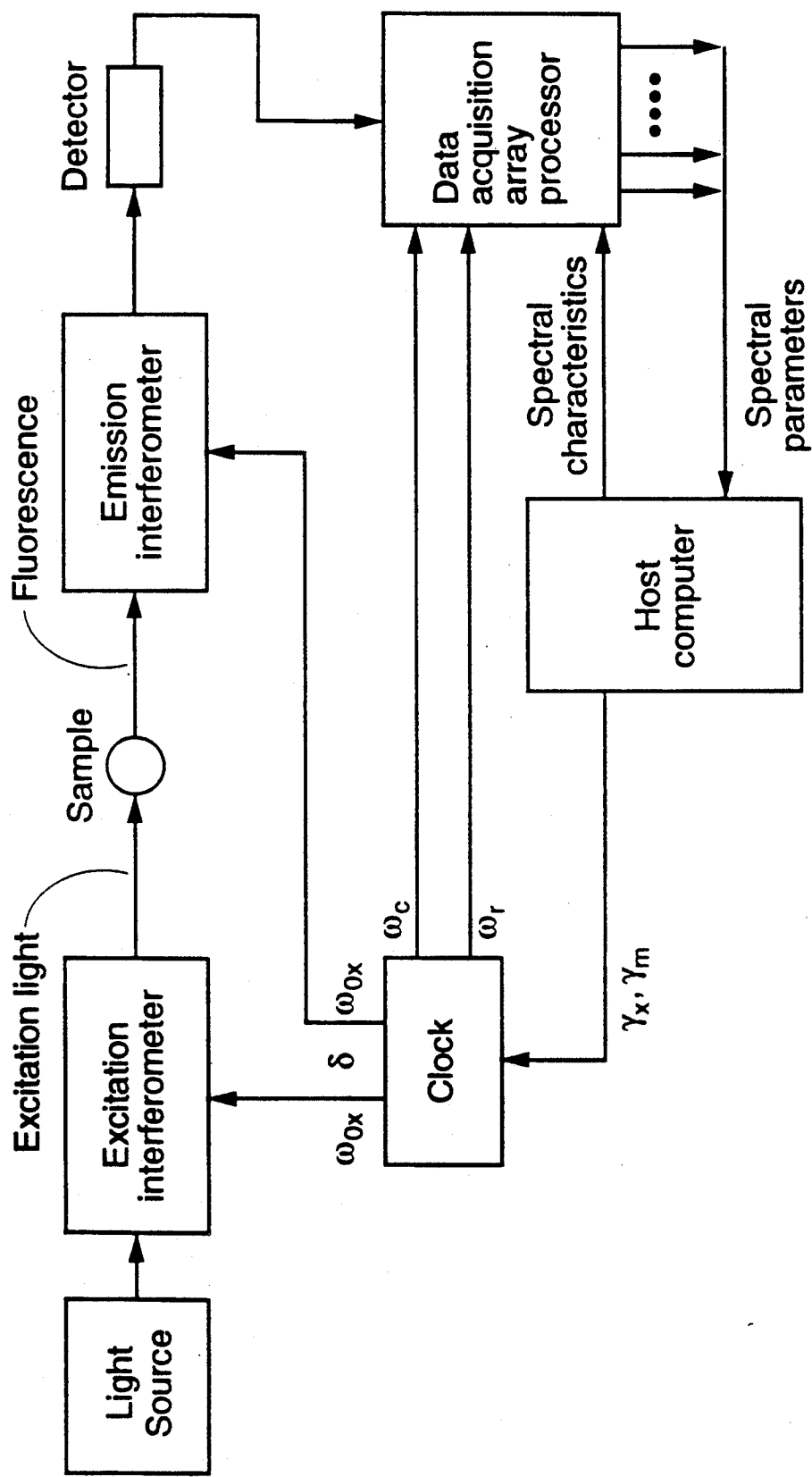
FIG. 2 shows a schematic representation of a generalized embodiment of the trivariate Fourier transform spectrometer of the present invention.

A block diagram of the trivariate Fourier transform spectrometer of the present invention is shown in FIG. 2. The principal components of the optical system are two interferometers placed in the excitation and emission paths, a polychromatic excitation light source, and a detector. A synchronization clock supplies four basic signals. (i) a driving signal for the excitation interferometer (angular frequency $\omega_{Ox}$); (ii) a driving signal for the emission interferometer (frequency $\omega_c$); and (iii) a reset signal for the index (address) generator (frequency $\omega_r$).

The four signals generated by the clock are phase-locked to each other. In a preferred embodiment, the following relationships obtain between the various frequencies:

$$\omega_{Ox} = n\omega_{Om}$$

$$\omega_c = m\omega_{Ox}$$

$$\omega_r = 2\omega_{Om}$$

The parameter, $\delta$, represents the adjustable difference between the initial phases of the two interferometer-driving signals. The data acquisition and processing system consists mainly of a data acquisition array processor and a host computer, organized in the manner previously described for emission FT cytometers. The host computer also controls the retardation amplitudes, $\gamma_x$ and $\gamma_m$, of the interferometers and, thus, the calibration of the instrument.

Figure 3:
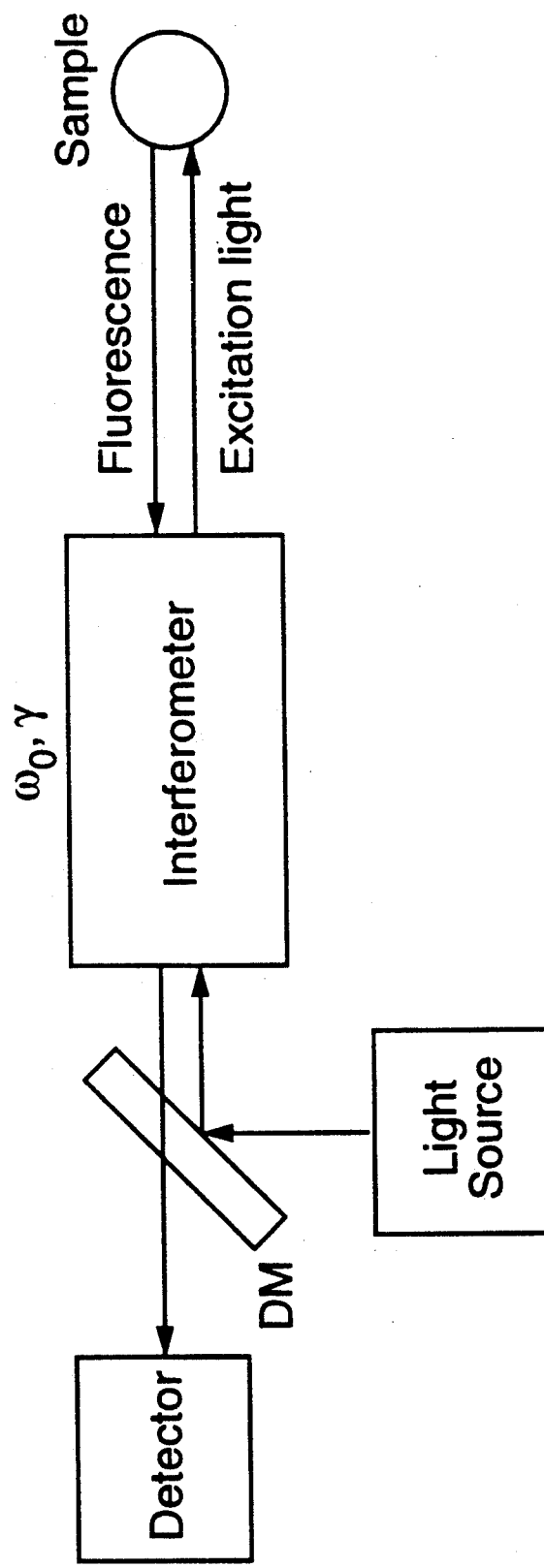
FIG. 3 shows a schematic representation of a reflex interferometer embodiment of the apparatus of the present invention.

A particularly simple embodiment of the trivariate Fourier transform spectrometer, which can be substituted in all applications, is the reflex interferometer shown in FIG. 3. This device uses a single interferometer driven at the frequency, $\omega_{Om}$, and with a retardation amplitude and $\gamma$. This is, obviously, equivalent to the complete device shown in FIGS. 1, 2, with the following parameters:

$$\omega_{Ox} = \omega_{Om} = \omega_O$$

$$\gamma_x = \gamma_m = \gamma$$

$$n = 1$$

The fact that the ratio of the driving frequencies, n, is equal to one results in higher-order terms of the point-response function that decrease more slowly.

Figure 4A:
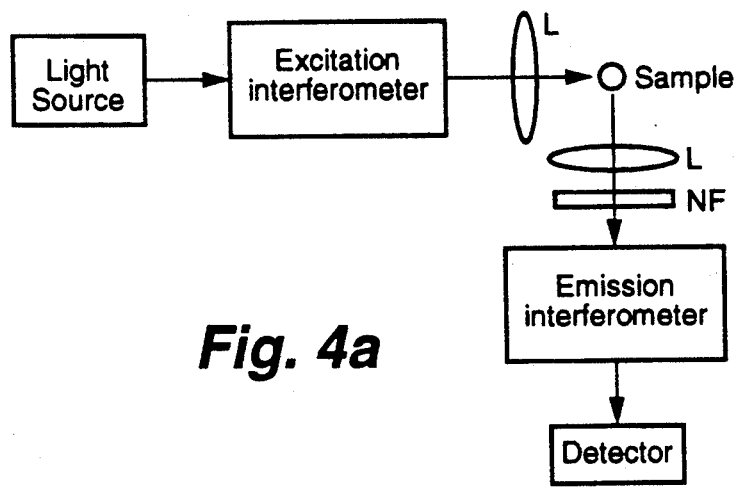
FIG. 4a showing the use in a flow cytometer where the sample is a particle in a stream of fluid.
Figure 4B:
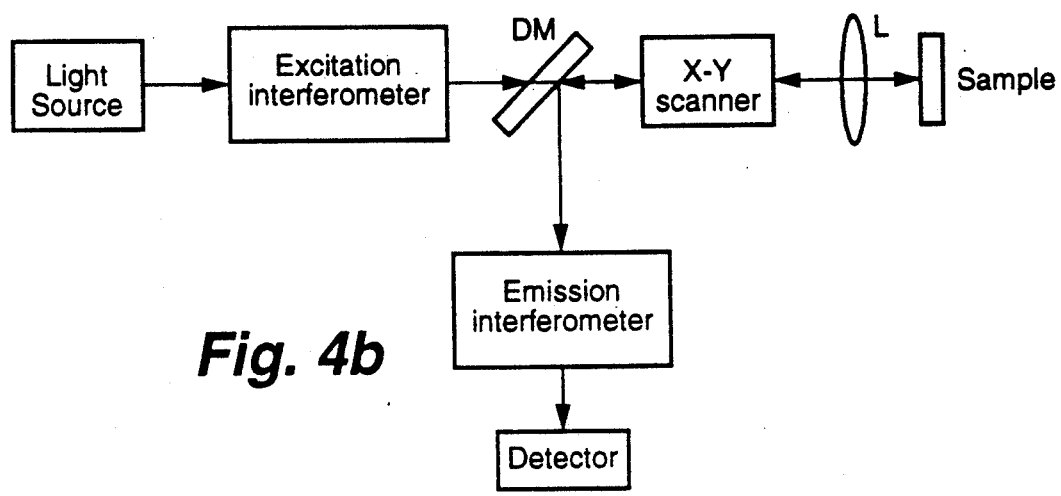
FIG. 4b showing the use in a laser-scan microscope, or in a flow cytometer.
Figure 4C:
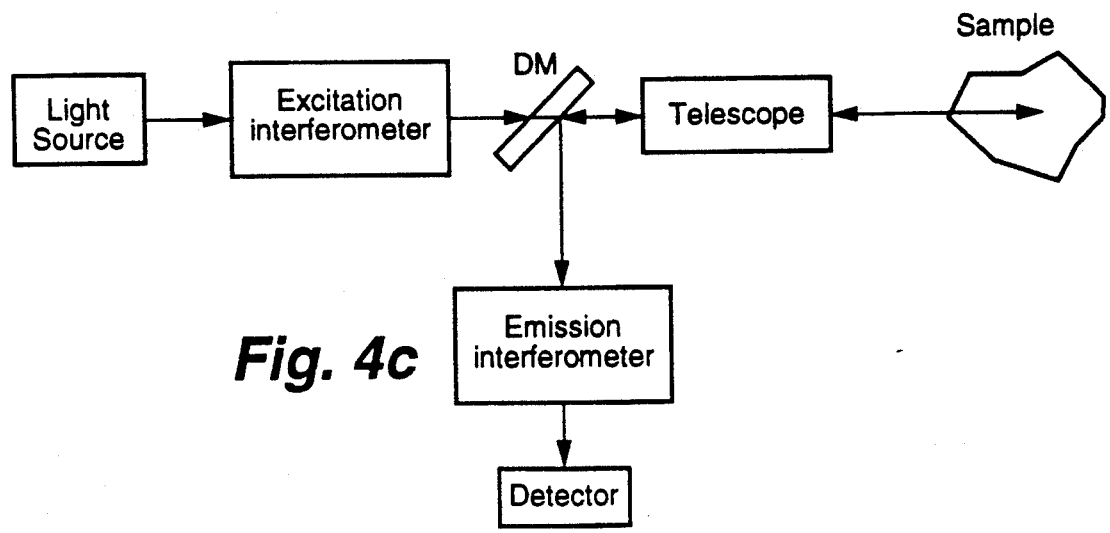
FIG. 4c showing the use for fluorescence lidar where the sample is a remote aerosol cloud.

Depending on the application, the trivariate Fourier transform spectrometer of FIG. 2 can be configured in several ways, which are shown in FIG. 4. The only difference among the various configurations lies in the excitation and collection optics. NF denotes a notch filter in FIG. 4a, while DM denotes a dichroic mirror in FIGS. 4b and 4c. L signifies lenses. The use of the notch filter and dichroic mirror will be set forth hereinbelow.

Having generally described the apparatus of the present invention, the following example will more particularly illustrate its features and method of its employment.

EXAMPLE

The practical requirements for the apparatus based on the proposed method follow from the point-response functions.

The spectral resolution of the method can be estimated from the point-response functions which yield the resolution values for the three variables of interest: $\delta\omega_x \approx \pi/\gamma_x$ for the excitation frequency; $\delta\tau_m \approx \pi/\gamma_m$ for the emission frequency; and $\delta\tau = \pi/\gamma_x\omega_x\omega_{Ox}$ for the fluorescence delay. For a value of the retardation amplitude of $\gamma = 1.27 \times 10^{14}$ s, a driving frequency, $\omega_{Ox} = 5.34 \times 10^5$ s$^{-1}$ (typical values for the interferometer on the existing FT flow cytometer), and an excitation wavelength of 488 nm, the following resolution values are obtained:

$$\delta\omega_x = \delta\omega_m = 2.47 \times 10^{14} \text{ s}^{-1} - 1.32 \times 10^3 \text{ cm}^{-1}$$

$$\delta\tau = 1.17 \times 10^{17} \text{ s}$$

These resolution values are appropriate for many biological applications, where the excitation and emission peaks are broad. The fluorescence delay resolution is rather low for most fluorochromes of biological interest, but an increase of about an order of magnitude can be obtained by increasing $\gamma_x$ through multiple passes of the excitation laser beam through the excitation interferometer. For lidar applications, the delay resolution above corresponds to a distance resolution of $$\delta D = c \, s/2 = 18 \text{ m}$$

which is more than adequate for most lidar applications, and which could be improved by up to an order of magnitude as discussed above.

For obvious practical reasons, there are some limitations as to the spectrum of the excitation light. Indeed, because of the necessity for preventing the scattered excitation light from reaching the fluorescence detectors, which is particularly important when measuring the fluorescence of microscopic particles, and because some of the excitation wavelengths may overlap with emission wavelengths, the excita spectrum must consist of several spectral lines, rather than being a continuum.

Consequently, a notch filter can be used in order to block only narrow regions of the spectrum around the excitation lines. In applications where the excitation and emission wavelengths must also be spatially separated (FIG. 3 and FIGS. 4b and 4c), a dichroic mirror that only reflects narrow spectral regions around the excitation wavelengths can be used (alternatively, the excitation and emission paths may be interchanged and use dichroic mirrors that have reflection properties complementary to the previous ones may be used).

The calibration of the trivariate Fourier transform spectrometer of the present invention can be easily performed in a manner similar to that used in the emission Fourier transform spectrometer of the above references. For example, a monochromatic laser beam of frequency, $\omega_c$, can be used for this purpose. If the scattered light filter is removed, the reconstructed spectral time-response function will show a set of maxima (because of the symmetry of the reconstructed function), the off-axis maxima being situated at a height, $\pm\omega_{mc}$, at a distance, $\omega_{xc}$ from the $\omega_3$ axis, and at an angle, $\delta$, relative to the $\omega_1$ axis. The retardation amplitudes, $\gamma_x$ and $\gamma_m$, can be adjusted and the function reconstructed until $\omega_{xc} = \omega_{mc} = \omega_c$. As $\delta$ is the phase lag of the excitation interferometer, this value of the phase lag can be used for reconstructing the spectral time-response function. Other modes of calibration are also possible.

The foregoing description of two preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for simultaneously measuring any combination of excitation, emission, and lifetime properties of the fluorescence from a sample, said apparatus comprising in combination:
  a. an excitation light source comprising a source of multiple-wavelength electromagnetic radiation and first interferometric means for receiving the electromagnetic radiation from said source of electromagnetic radiation, and having as the output thereof a chosen plurality of excitation wavelengths, each excitation wavelength being modulated at a multiplicity of frequencies different from those of other wavelengths within the plurality thereof, said first interferometric means being driven at a chosen first driving frequency, the output being directed into the sample;
  b. second interferometric means for receiving electromagnetic radiation emitted from the sample resulting from the interaction thereof with the plurality of excitation wavelengths output from said first interferometric means, and for introducing modulation into the received emitted electromagnetic radiation, such that each received wavelength is modulated at a multiplicity of frequencies different from those of other received wavelengths before appearing as an output therefrom, said second interferometric means being driven at a chosen second driving frequency and having a chosen phase relationship with the first driving frequency;
  c. detection means for receiving the output from said second interferometric means and generating an electrical signal therefrom; and
  d. means for analyzing the electrical signal from said detection means and for deriving therefrom any combination of the fluorescence properties of the sample.

2. The apparatus as described in claim 1, wherein said first interferometric means and said second interferometric means comprise in combination:
  a. a first polarizer for receiving electromagnetic radiation having an electric field disposed in an arbitrary direction and for defining a first direction for the electric field of the electromagnetic radiation transmitted therethrough;
  b. modulatable birefringent means for receiving the transmitted polarized electromagnetic radiation from said first polarizer, said birefringent means having first and second optical axes along which the electric field of the transmitted polarized electromagnetic radiation is resolved into two components, the light wave corresponding to each of the electric field components traveling at a different velocity such that two first light waves emerge from said birefringent means having different electric field directions and a shift in phase greater than one wavelength of the longest wavelength component of the electromagnetic radiation;
  c. a second polarizer for receiving the two first light waves emerging from said birefringent means and resolving the electric fields thereof along a second direction such that two second light waves emerge plane polarized and with the same direction of polarization; and
  d. means for modulating said birefringent means such that a chosen resolution is achieved.

3. The apparatus as described in claim 1, wherein said first interferometer means and said second interferometer means comprise in combination:
  a. modulatable birefringent means for receiving substantially polarized electromagnetic radiation having an electric field disposed in a particular direction, said birefringent means having first and second optical axes along which the electric field of the electromagnetic radiation is resolved into two components, the light wave corresponding to each of the resolved electric field components traveling at a different velocity such that two first light waves emerge from said birefringent means having different electric field directions and a shift in phase greater than one wavelength of the longest wavelength component of the electromagnetic radiation;
  b. a polarizer for receiving the two first light waves emerging from said birefringent means and resolving the electric fields thereof along a second direction such that two second light waves emerge plane polarized and with the same direction of polarization; and
  c. means for modulating said birefringent means such that a chosen resolution is achieved.

4. An apparatus for simultaneously measuring any combination of excitation, emission, and lifetime properties of the fluorescence from a sample, said apparatus comprising in combination:

a. an excitation light source comprising a source of multiple-wavelength electromagnetic radiation;

b. interferometric means for receiving the electromagnetic radiation from said source of electromagnetic radiation, and having as the output thereof a chosen plurality of excitation wavelengths, each excitation wavelength being modulated at a multiplicity of frequencies different from those of other wavelengths within the plurality thereof, said interferometric means being driven at a chosen driving frequency, the output being directed into the sample;

c. means for directing electromagnetic radiation emitted from the sample resulting from the interaction thereof with the plurality of excitation wavelengths output from said interferometric means into said interferometric means for introducing modulation into the emitted electromagnetic radiation received by said interferometric means, such that each received wavelength is modulated at a multiplicity of frequencies different from those of other received wavelengths before appearing as an output therefrom;

d. detection means for receiving the output from said interferometric means and generating an electrical signal therefrom; and e. means for analyzing the electrical signal from said detection means and for deriving therefrom any combination of the fluorescence properties of the sample.

5. The apparatus as described in claim 4, wherein said interferometric means comprises in combination:

a. a first polarizer for receiving electromagnetic radiation having an electric field disposed in an arbitrary direction and for defining a first direction for the electric field of the electromagnetic radiation transmitted therethrough;

b. modulatable birefringent means for receiving the transmitted polarized electromagnetic radiation from said first polarizer, said birefringent means having first and second optical axes along which the electric field of the transmitted polarized electromagnetic radiation is resolved into two components, the light wave corresponding to each of the electric field components traveling at a different velocity such that two first light waves emerge from said birefringent means having different electric field directions and a shift in phase greater than one wavelength of the longest wavelength component of the electromagnetic radiation;

c. a second polarizer for receiving the two first light waves emerging from said birefringent means and resolving the electric fields thereof along a second direction such that two second light waves emerge plane polarized and with the same direction of polarization; and d. means for modulating said birefringent means such that a chosen resolution is achieved.

6. The apparatus as described in claim 4, wherein said interferometer means comprises in combination:

a. modulatable birefringent means for receiving substantially polarized electromagnetic radiation having an electric field disposed in a particular direction, said birefringent means having first and second optical axes along which the electric field of the electromagnetic radiation is resolved into two components, the light wave corresponding to each of the resolved electric field components traveling at a different velocity such that two first light waves emerge from said birefringent means having different electric field directions and a shift in phase greater than one wavelength of the longest wavelength component of the electromagnetic radiation;

b. a polarizer for receiving the two first light waves emerging from said birefringent means and resolving the electric fields thereof along a second direction such that two second light waves emerge plane polarized and with the same direction of polarization; and c. means for modulating said birefringent means such that a chosen resolution is achieved.

7. An apparatus for simultaneously measuring any combination of excitation, emission, and lifetime properties of the fluorescence from individual particles, said apparatus comprising in combination:

a. an excitation light source comprising a source of multiple-wavelength electromagnetic radiation and first interferometric means for receiving the electromagnetic radiation from said source of electromagnetic radiation, and having as the output thereof a chosen plurality of excitation wavelengths, each excitation wavelength being modulated at a multiplicity of frequencies different from those of other wavelengths within the plurality thereof, said first interferometric means being driven at a chosen first driving frequency, the output being directed into the particles under investigation;

b. means for directing the output sequentially onto individual particles;

c. second interferometric means for receiving electromagnetic radiation emitted from individual particles resulting from the interaction thereof with the plurality of excitation wavelengths output from said first interferometric means, and for introducing modulation into the received emitted electromagnetic radiation, such that each received wavelength is modulated at a multiplicity of frequencies different from those of other received wavelengths before appearing as an output therefrom, said second interferometric means being driven at a chosen second driving frequency and having a chosen phase relationship with the first driving frequency;

d. detection means for receiving the output from said second interferometric means and generating an electrical signal therefrom; and e. means for analyzing the electrical signal from said detection means and for deriving therefrom any combination of the fluorescence properties of the individual particles.

8. The apparatus as described in claim 7, wherein said first interferometric means and said second interferometric means comprise in combination:

a. a first polarizer for receiving electromagnetic radiation having an electric field disposed in an arbitrary direction and for defining a first direction for the electric field of the electromagnetic radiation transmitted therethrough;

b. modulatable birefringent means for receiving the transmitted polarized electromagnetic radiation from said first polarizer, said birefringent means having first and second optical axes along which the electric field of the transmitted polarized electromagnetic radiation is resolved into two components, the light wave corresponding to each of the electric field components traveling at a different velocity such that two first light waves emerge from said birefringent means having different electric field directions and a shift in phase greater than one wavelength of the longest wavelength component of the electromagnetic radiation;

c. a second polarizer for receiving the two first light waves emerging from said birefringent means and resolving the electric fields thereof along a second direction such that two second light waves emerge plane polarized and with the same direction of polarization; and d. means for modulating said birefringent means such that a chosen resolution is achieved.

9. The apparatus as described in claim 7, wherein said first interferometer means and said second interferometer means comprise in combination:

a. modulatable birefringent means for receiving substantially polarized electromagnetic radiation having an electric field disposed in a particular direction, said birefringent means having first and second optical axes along which the electric field of the electromagnetic radiation is resolved into two components, the light wave corresponding to each of the resolved electric field components traveling at a different velocity such that two first light waves emerge from said birefringent means having different electric field directions and a shift in phase greater than one wavelength of the longest wavelength component of the electromagnetic radiation;

b. a polarizer for receiving the two first light waves emerging from said birefringent means and resolving the electric fields thereof along a second direction such that two second light waves emerge plane polarized and with the same direction of polarization; and c. means for modulating said birefringent means such that a chosen resolution is achieved.

10. An apparatus for simultaneously measuring any combination of excitation, emission, and lifetime properties of the fluorescence from a remote assembly of particles, said apparatus comprising in combination:

a. an excitation light source comprising a source of multiple-wavelength electromagnetic radiation and first interferometric means for receiving the electromagnetic radiation from said source of electromagnetic radiation, and having as the output thereof a chosen plurality of excitation wavelengths, each excitation wavelength being modulated at a multiplicity of frequencies different from those of other wavelengths within the plurality thereof, said first interferometric means being driven at a chosen first driving frequency, the output being directed into the particles under investigation;

b. telescope means for collecting electromagnetic radiation emitted from the particles resulting from the interaction thereof with the plurality of excitation wavelengths output from said first interferometric means;

c. second interferometric means for receiving the light collected by said telescope means and for introducing modulation into the received collected electromagnetic radiation, such that each received wavelength is modulated at a multiplicity of frequencies different from those of other received wavelengths before appearing as an output therefrom, said second interferometric means being driven at a chosen second driving frequency and having a chosen phase relationship with the first driving frequency;

d. detection means for receiving the output from said second interferometric means and generating an electrical signal therefrom; and e. means for analyzing the electrical signal from said detection means and for deriving therefrom any combination of the fluorescence properties of the assembly of particles.

11. The apparatus as described in claim 10, wherein said first interferometric means and said second interferometric means comprise in combination:

a. a first polarizer for receiving electromagnetic radiation having an electric field disposed in an arbitrary direction and for defining a first direction for the electric field of the electromagnetic radiation transmitted therethrough;

b. modulatable birefringent means for receiving the transmitted polarized electromagnetic radiation from said first polarizer, said birefringent means having first and second optical axes along which the electric field of the transmitted polarized electromagnetic radiation is resolved into two components, the light wave corresponding to each of the electric field components traveling at a different velocity such that two first light waves emerge from said birefringent means having different electric field directions and a shift in phase greater than one wavelength of the longest wavelength component of the electromagnetic radiation;

c. a second polarizer for receiving the two first light waves emerging from said birefringent means and resolving the electric fields thereof along a second direction such that two second light waves emerge plane polarized and with the same direction of polarization; and d. means for modulating said birefringent means such that a chosen resolution is achieved.

12. The apparatus as described in claim 10, wherein said first interferometer means and said second interferometer means comprise in combination:

a. modulatable birefringent means for receiving substantially polarized electromagnetic radiation having an electric field disposed in a particular direction, said birefringent means having first and second optical axes along which the electric field of the electromagnetic radiation is resolved into two components, the light wave corresponding to each of the resolved electric field components traveling at a different velocity such that two first light waves emerge from said birefringent means having different electric field directions and a shift in phase greater than one wavelength of the longest wavelength component of the electromagnetic radiation;

b. a polarizer for receiving the two first light waves emerging from said birefringent means and resolving the electric fields thereof along a second direction such that two second light waves emerge plane polarized and with the same direction of polarization; and c. means for modulating said birefringent means such that a chosen resolution is achieved.

13. An apparatus for simultaneously measuring any combination of excitation, emission, and lifetime properties of the fluorescence from a microscopic assembly of pixels, said apparatus comprising in combination:

a. an excitation light source comprising a source of multiple-wavelength electromagnetic radiation and first interferometric means for receiving the electromagnetic radiation from said source of electromagnetic radiation, and having as the output thereof a chosen plurality of excitation wavelengths, each excitation wavelength being modulated at a multiplicity of frequencies different from those of other wavelengths within the plurality thereof, said first interferometric means being driven at a chosen first driving frequency;

b. microscope means for directing the plurality of excitation wavelengths output from said first interferometric means into the microscopic assembly of pixels under investigation and for collecting electromagnetic radiation emitted from the pixel assembly resulting from the interaction thereof with the plurality of excitation wavelengths output from said first interferometric means;

c. second interferometric means for receiving the light collected by said telescope means and for introducing modulation into the received collected electromagnetic radiation, such that each received wavelength is modulated at a multiplicity of frequencies different from those of other received wavelengths before appearing as an output therefrom, said second interferometric means being driven at a chosen second driving frequency and having a chosen phase relationship with the first driving frequency;

d. detection means for receiving the output from said second interferometric means and generating an electrical signal therefrom; and e. means for analyzing the electrical signal from said detection means and for deriving therefrom any combination of the fluorescence properties of the assembly of pixels.

14. The apparatus as described in claim 13, wherein said first interferometric means and said second interferometric means comprise in combination:

a. a first polarizer for receiving electromagnetic radiation having an electric field disposed in an arbitrary direction and for defining a first direction for the electric field of the electromagnetic radiation transmitted therethrough;

b. modulatable birefringent means for receiving the transmitted polarized electromagnetic radiation from said first polarizer, said birefringent means having first and second optical axes along which the electric field of the transmitted polarized electromagnetic radiation is resolved into two components, the light wave corresponding to each of the electric field components traveling at a different velocity such that two first light waves emerge from said birefringent means having different electric field directions and a shift in phase greater than one wavelength of the longest wavelength component of the electromagnetic radiation;

c. a second polarizer for receiving the two first light waves emerging from said birefringent means and resolving the electric fields thereof along a second direction such that two second light waves emerge plane polarized and with the same direction of polarization; and d. means for modulating said birefringent means such that a chosen resolution is achieved.

15. The apparatus as described in claim 13, wherein said first interferometer means and said second interferometer means comprise in combination:

a. modulatable birefringent means for receiving substantially polarized electromagnetic radiation having an electric field disposed in a particular direction, said birefringent means having first and second optical axes along which the electric field of the electromagnetic radiation is resolved into two components, the light wave corresponding to each of the resolved electric field components traveling at a different velocity such that two first light waves emerge from said birefringent means having different electric field directions and a shift in phase greater than one wavelength of the longest wavelength component of the electromagnetic radiation;

b. a polarizer for receiving the two first light waves emerging from said birefringent means and resolving the electric fields thereof along a second direction such that two second light waves emerge plane polarized and with the same direction of polarization; and c. means for modulating said birefringent means such that a chosen resolution is achieved.

16. A method for simultaneously measuring any combination of excitation, emission, and lifetime properties of the steps of:

a. exciting the sample with electromagnetic radiation having a chosen plurality of excitation wavelengths, each excitation wavelength being modulated at a multiplicity of frequencies different from those of other wavelengths within the plurality thereof;

b. collecting the light emitted from the sample resulting from the interaction thereof with the plurality of excitation wavelengths;

c. introducing modulation into the collected emitted electromagnetic radiation, such that each collected wavelength is modulated at a multiplicity of frequencies different from those of other collected wavelengths;

d. detecting the modulated collected emitted electromagnetic radiation and generating an electrical signal therefrom; and e. analyzing the electrical signal to derive therefrom any combination of the fluorescence properties of the sample.

17. A method for simultaneously measuring any combination of excitation, emission, and lifetime properties of the fluorescence from individual particles, said method comprising the steps of:

a. sequentially directing onto individual particles electromagnetic radiation having a chosen plurality of excitation wavelengths, each excitation wavelength being modulated at a multiplicity of frequencies different from those of other wavelengths within the plurality thereof;

b. collecting the electromagnetic radiation emitted from individual particles resulting from the interaction thereof with the plurality of excitation wavelengths;

c. introducing modulation into the collected emitted electromagnetic radiation, such that each collected wavelength is modulated at a multiplicity of frequencies different from those of other collected wavelengths;

d. detecting the modulated collected emitted electromagnetic radiation and generating an electrical signal therefrom; and e. analyzing the electrical signal to derive therefrom any combination of the fluorescence properties of the individual particles.

* * * * *